(12) United States Patent
Lamego et al.

(10) Patent No.: US 8,830,449 B1
(45) Date of Patent: Sep. 9, 2014

(54) BLOOD ANALYSIS SYSTEM

(75) Inventors: Marcelo M. Lamego, Coto de Caza, CA (US); Cristiano Dalvi, Lake Forest, CA (US); Hung The Vo, Fountain Valley, CA (US); Sean Merrit, Lake Forest, CA (US); Greg A. Olsen, Trabuco Canyon, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 144 days.

(21) Appl. No.: 13/449,307

(22) Filed: Apr. 17, 2012

Related U.S. Application Data

(60) Provisional application No. 61/476,512, filed on Apr. 18, 2011.

(51) Int. Cl.
*G01N 33/48* (2006.01)
*G01N 33/49* (2006.01)
*G01N 15/05* (2006.01)

(52) U.S. Cl.
CPC ............... *G01N 33/49* (2013.01); *G01N 15/05* (2013.01)
USPC ............................................. 356/39; 356/40

(58) Field of Classification Search
CPC .................................................... G01N 33/49
USPC ........................................................ 356/39–42
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |

(Continued)

*Primary Examiner* — Michael P Stafira
(74) *Attorney, Agent, or Firm* — Knobbe Martens Olson & Bear LLP

(57) ABSTRACT

A blood analysis system functions as a non-invasive blood parameter analyzer when a monitor is coupled with an optical sensor and as an invasive blood sample analyzer when the monitor is coupled with a blood analysis adapter. The blood analysis adapter has a transmitting assembly and a receiving assembly in electrical communications with the adapter connector so as to receive emitter signals for driving emitters within the transmitting assembly and so as to transmit a detector signal for responding to at least one detector in the receiving assembly. A cuvette containing a blood sample is irradiated with multiple wavelength light from the emitters, the detector responds to the multiple wavelength light after attenuation by the blood sample, and the monitor analyzes the blood sample according to the detector signal.

14 Claims, 19 Drawing Sheets

(56) References Cited

U.S. PATENT DOCUMENTS

| | | |
|---|---|---|
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |

(56) References Cited

U.S. PATENT DOCUMENTS

| | | |
|---|---|---|
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,255,026 B1 | 8/2012 | Al-Ali |
| 8,255,028 B2 | 8/2012 | Al-Ali et al. |
| 8,260,577 B2 | 9/2012 | Weber et al. |
| 8,274,360 B2 | 9/2012 | Sampath et al. |
| 8,571,619 B2 * | 10/2013 | Al-Ali et al. ............ 600/322 |
| 2002/0123677 A1 * | 9/2002 | Miki et al. ............ 600/316 |

* cited by examiner

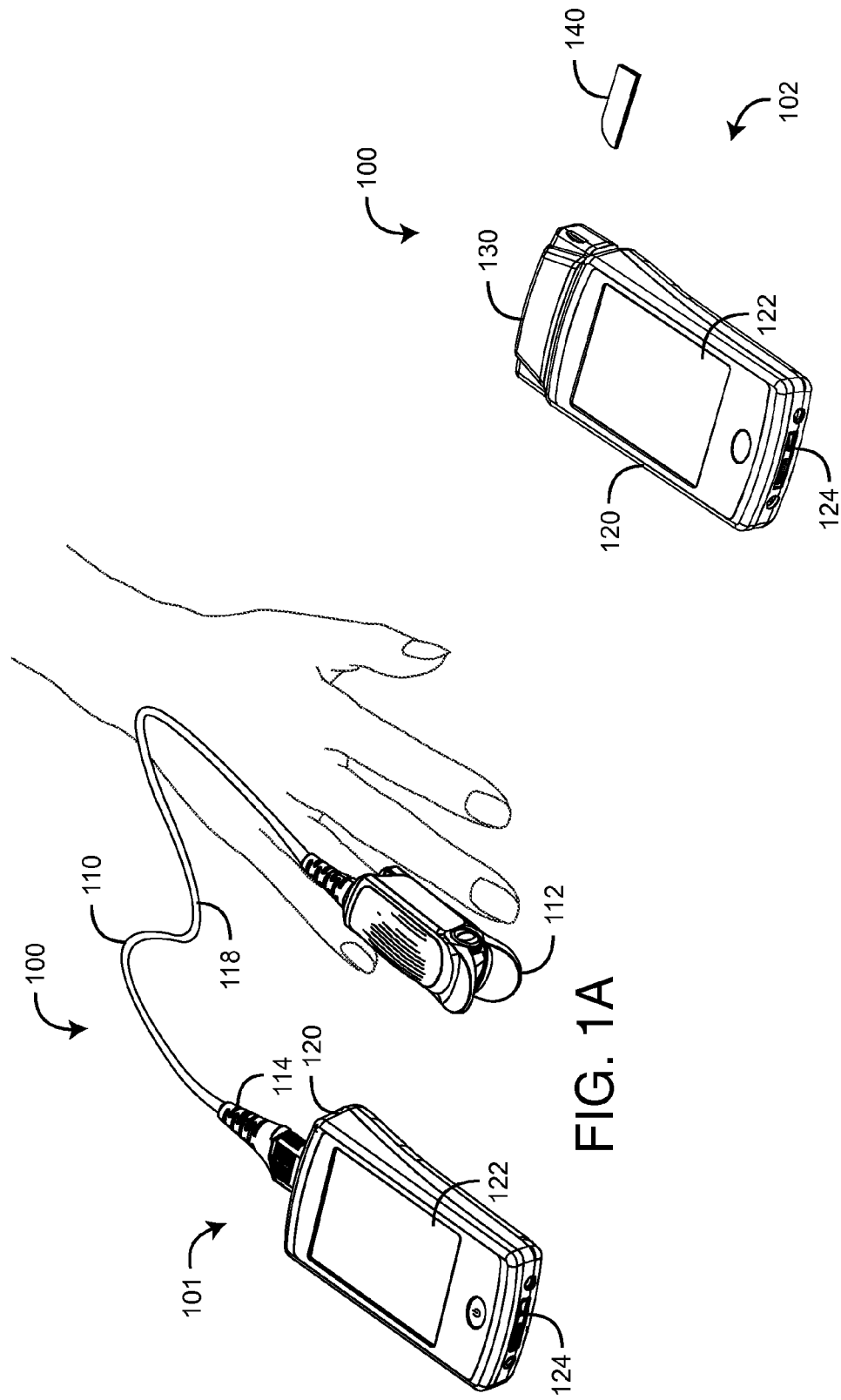

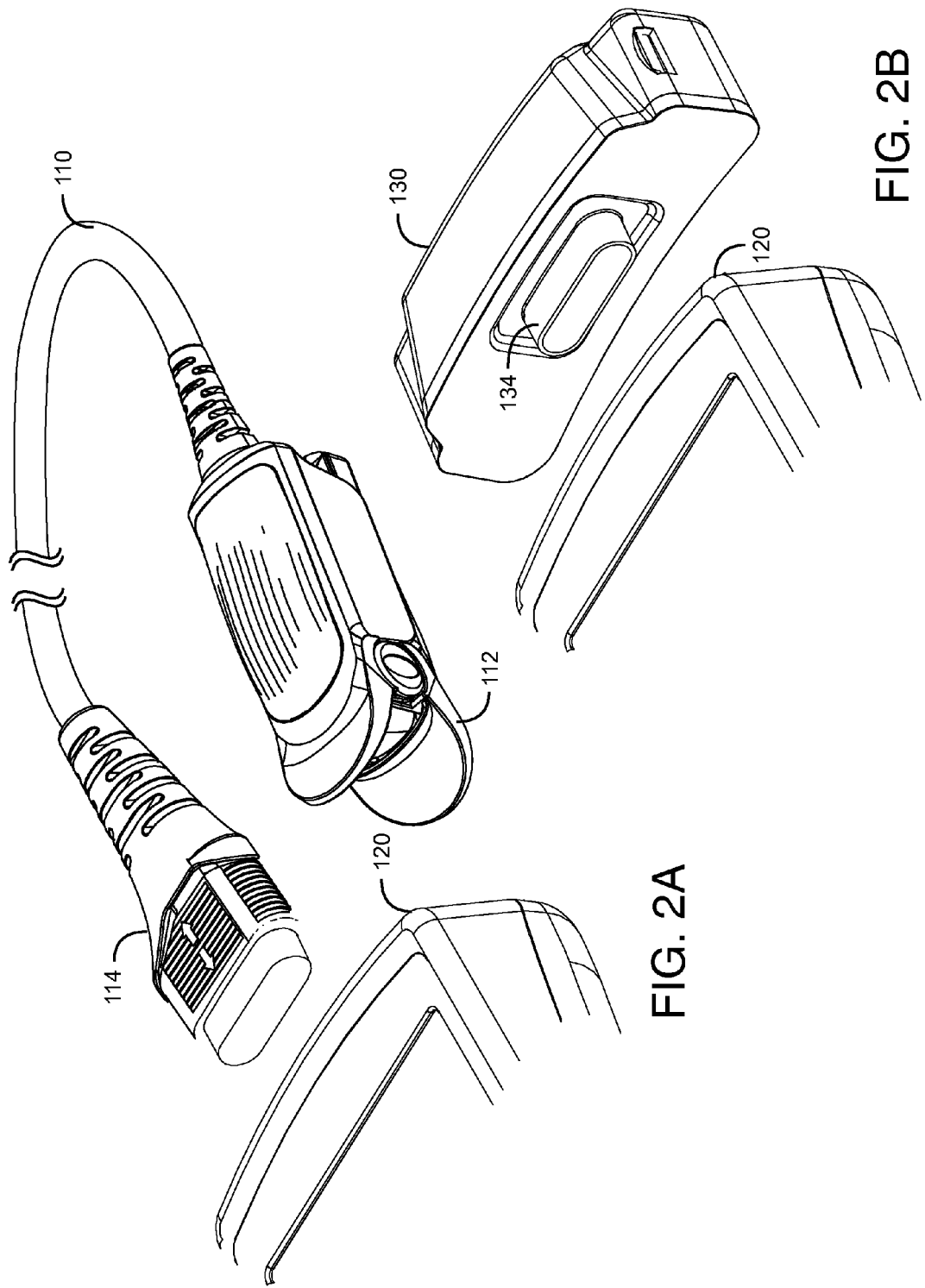

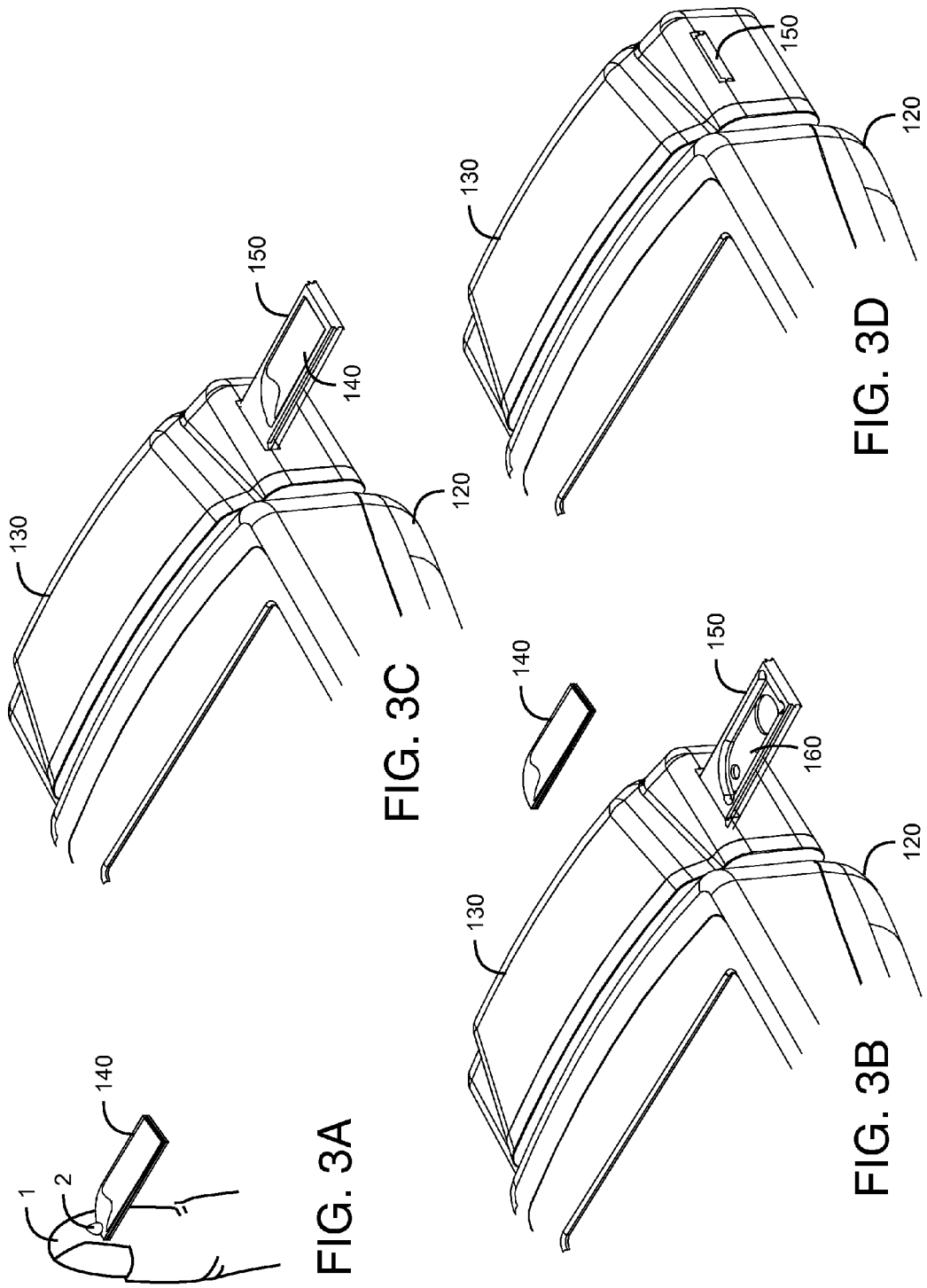

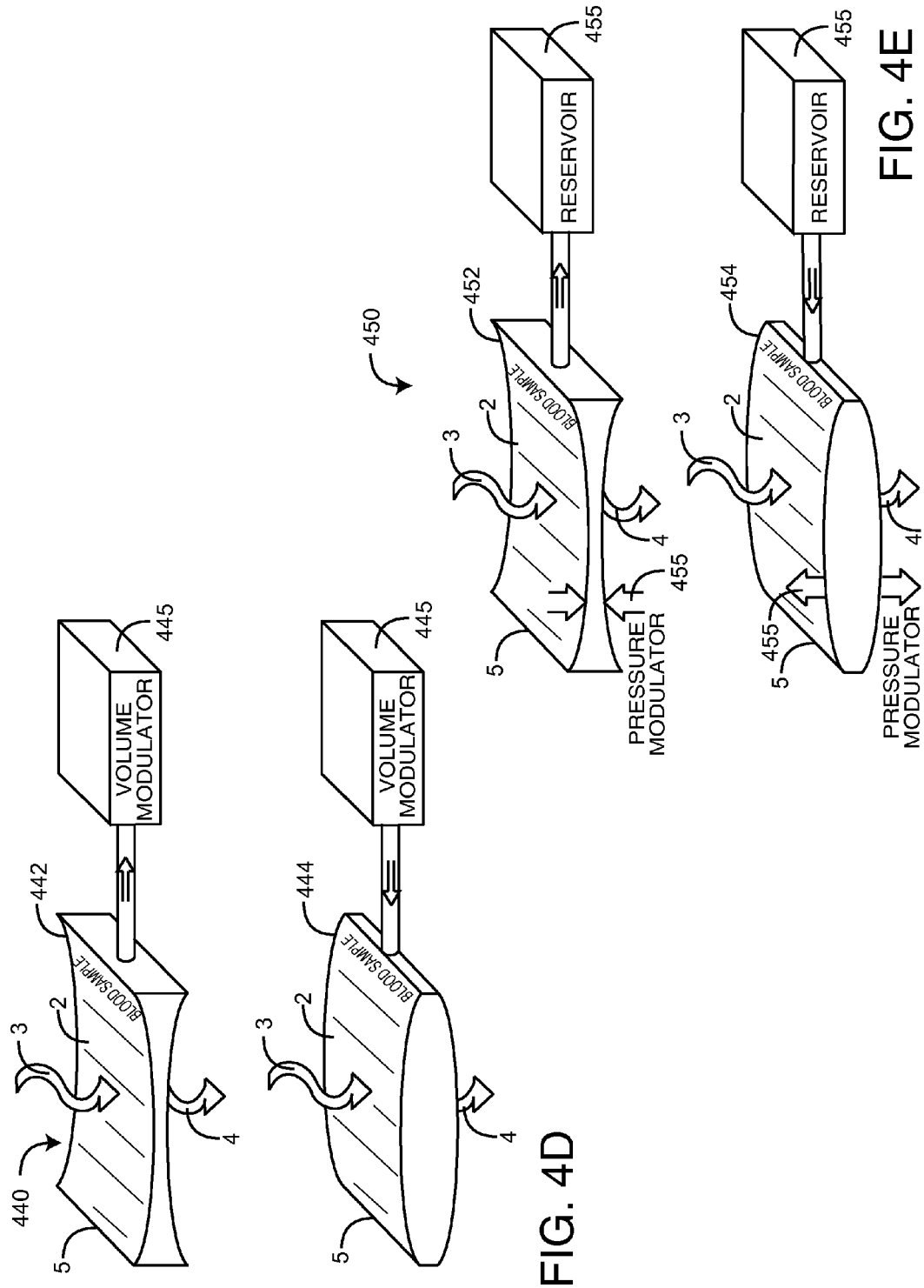

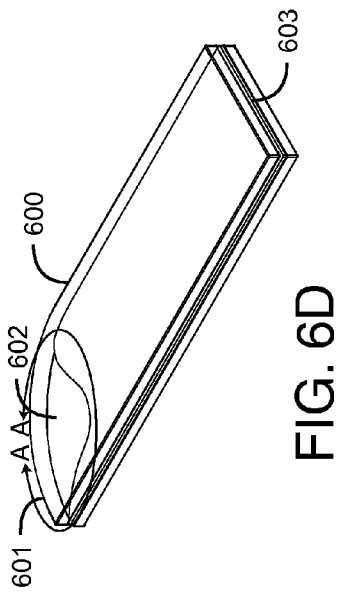
FIG. 6A
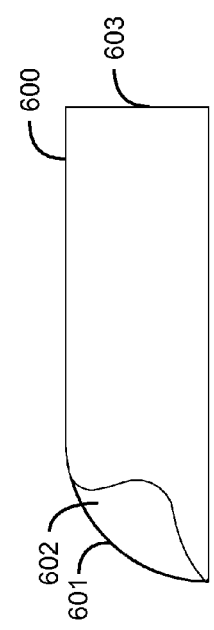
FIG. 6B
FIG. 6C
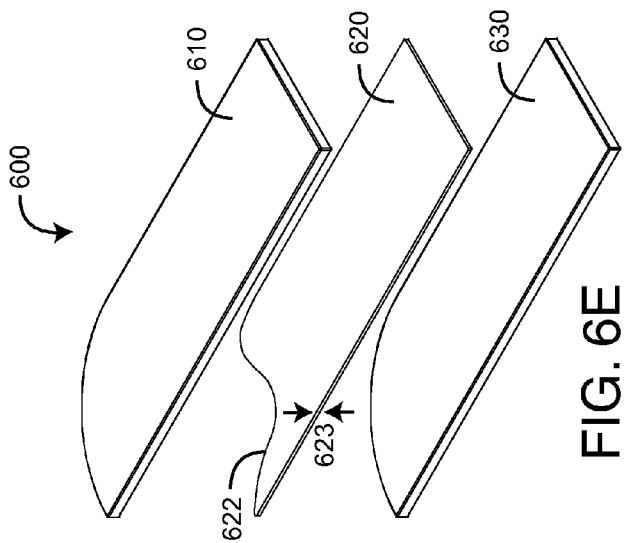
FIG. 6D
FIG. 6E
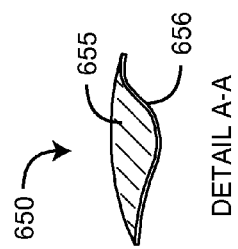
DETAIL A-A
FIG. 6F

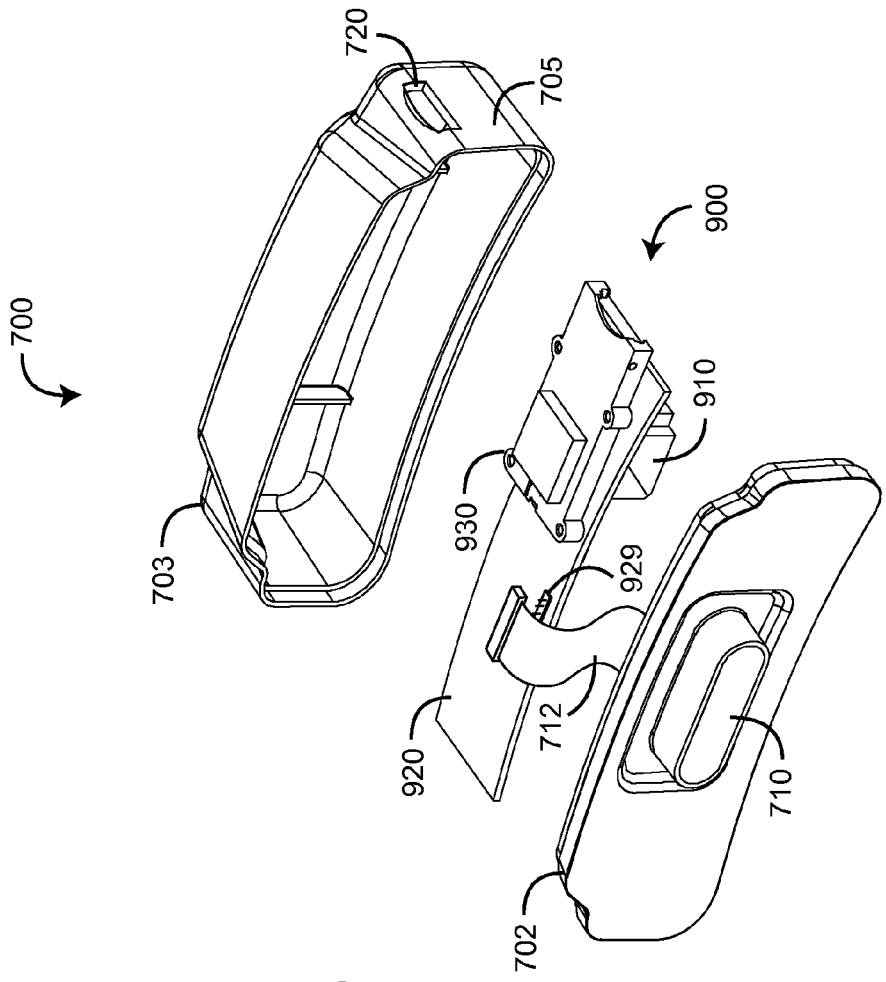
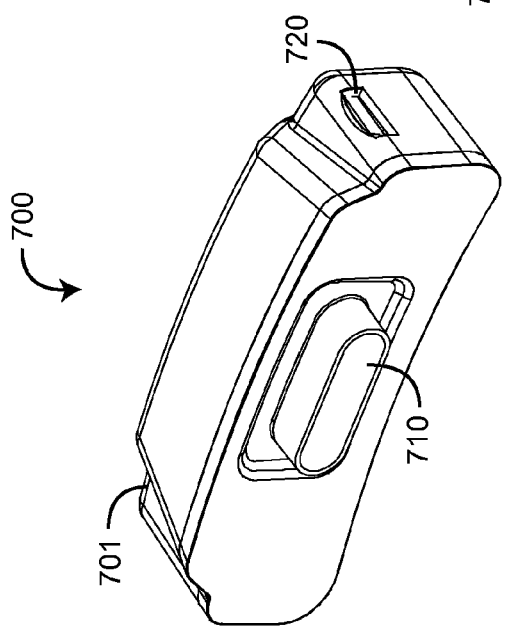
FIG. 7B
FIG. 7A

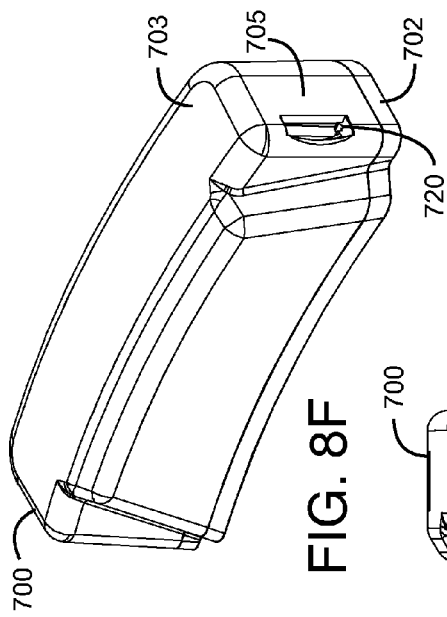
FIG. 8F
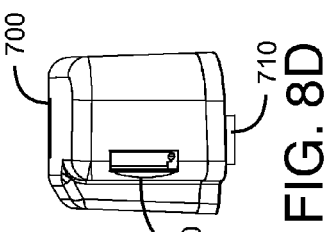
FIG. 8D
FIG. 8A
FIG. 8C
FIG. 8E
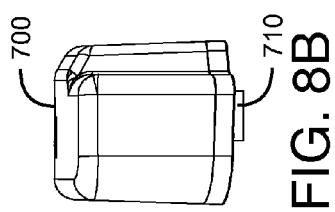
FIG. 8B

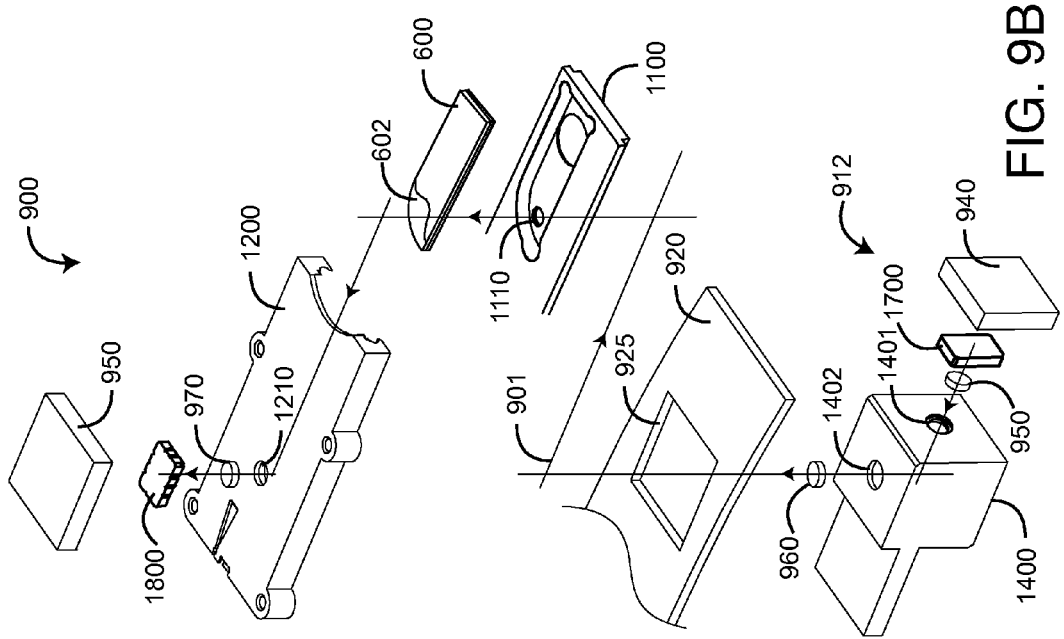
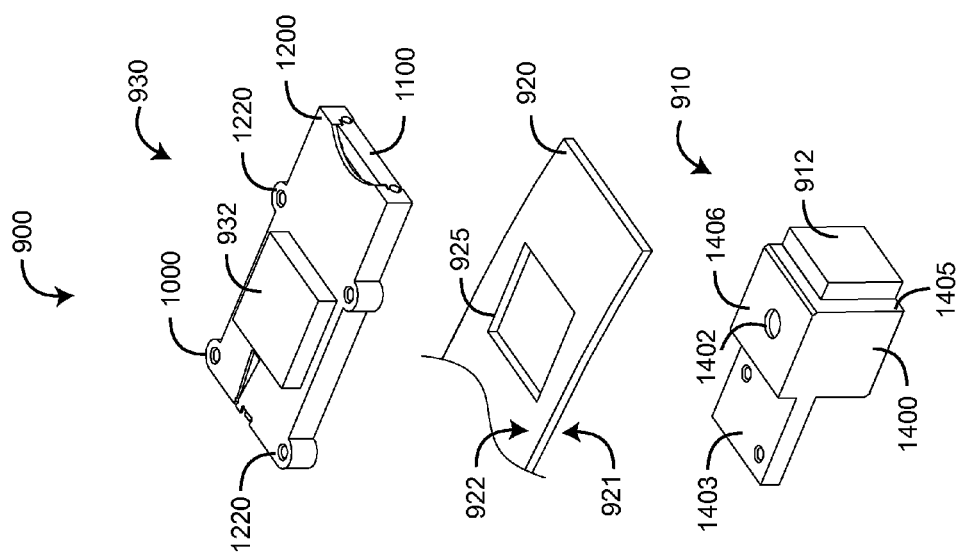

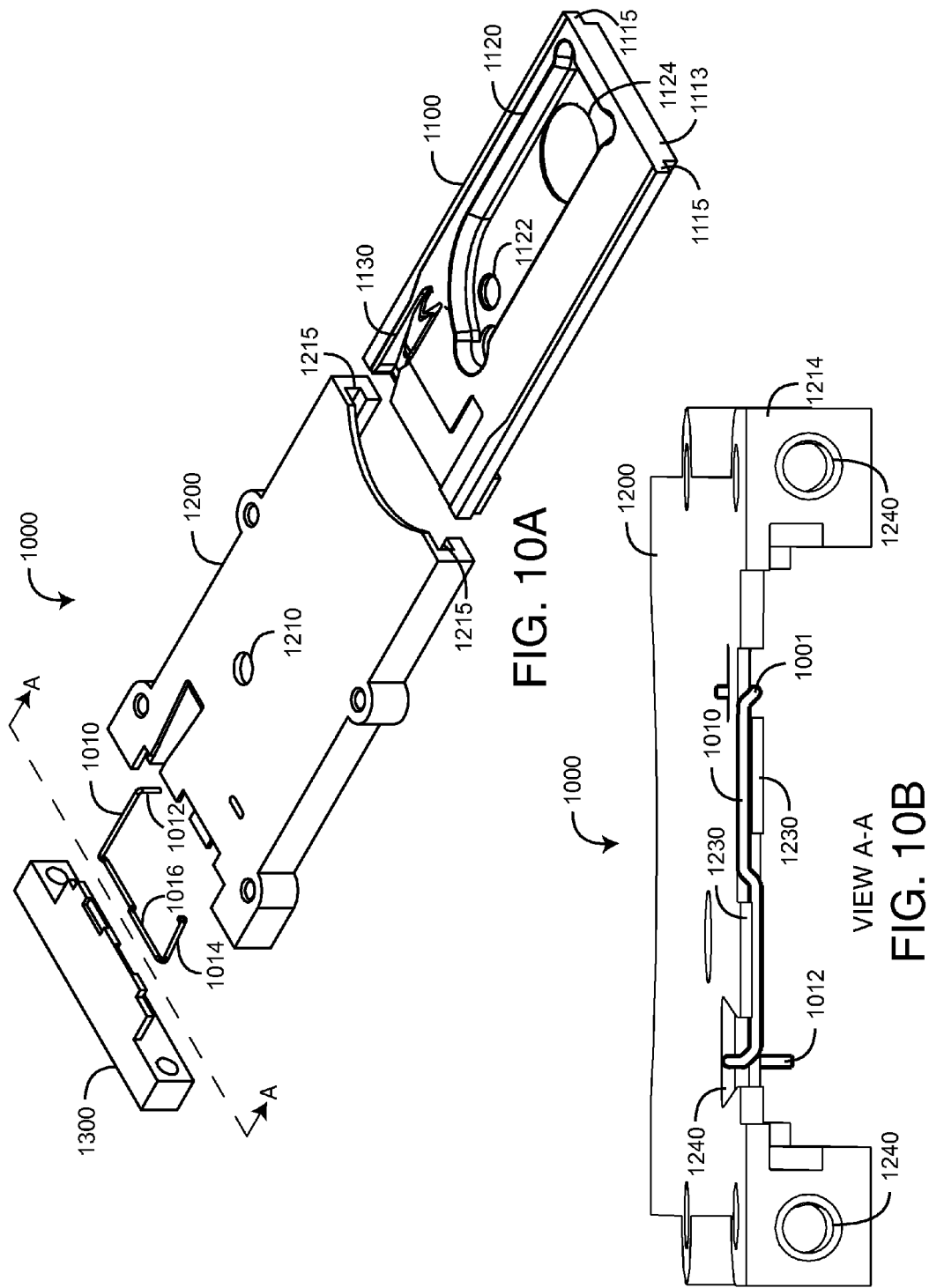

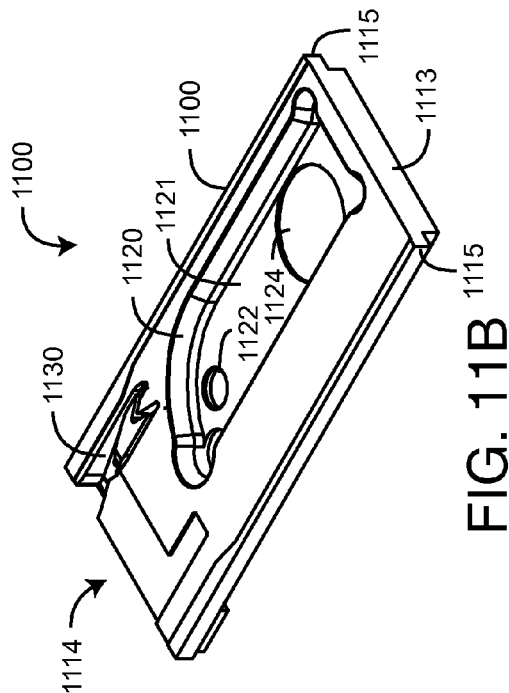
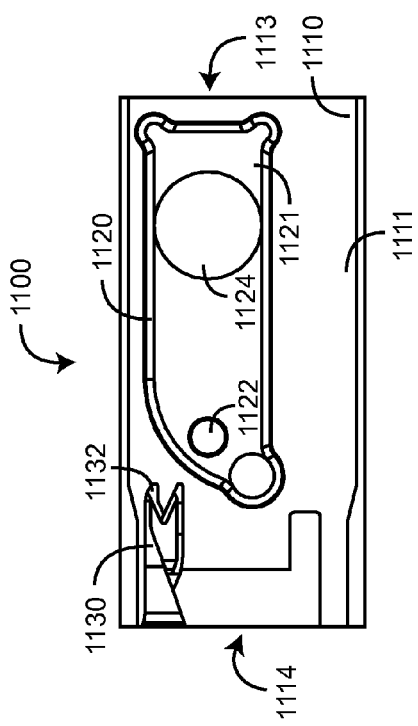
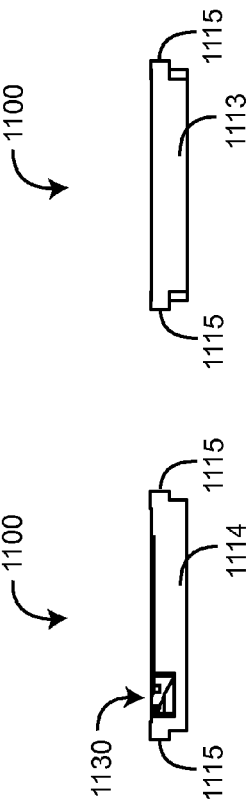
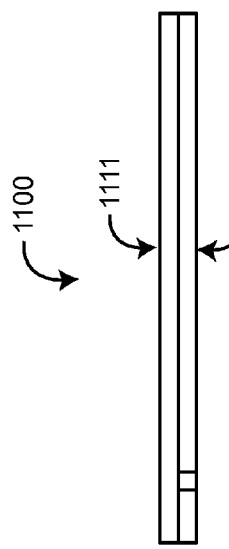

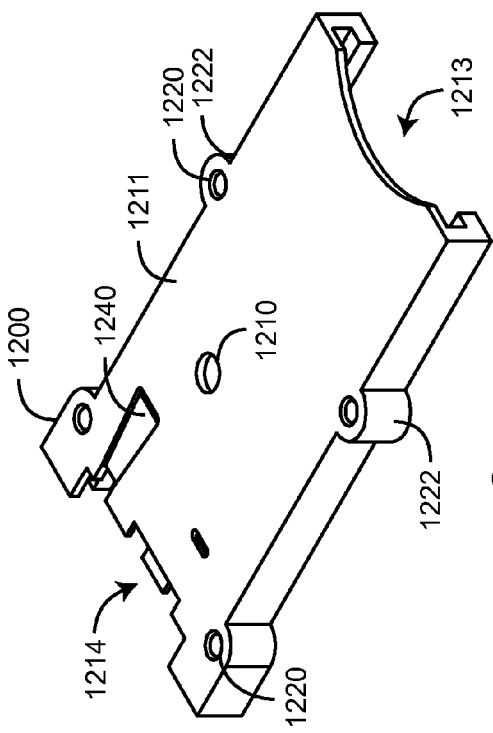
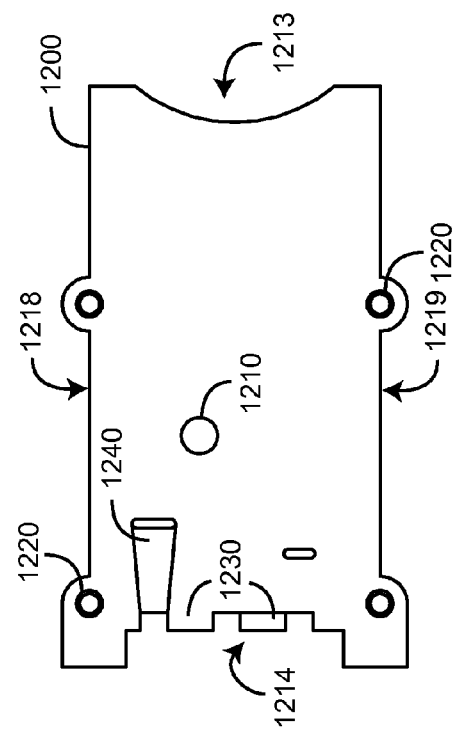
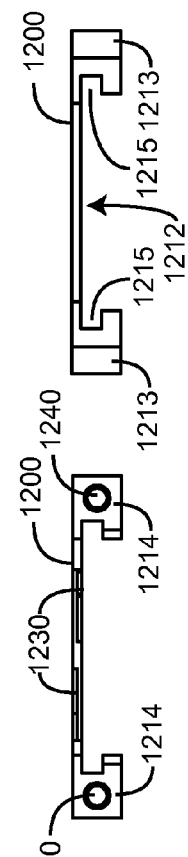
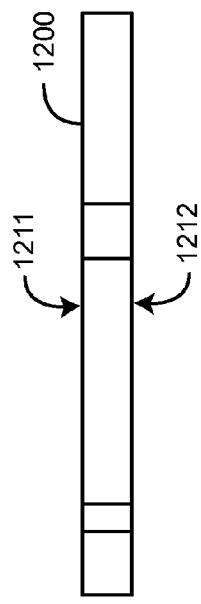

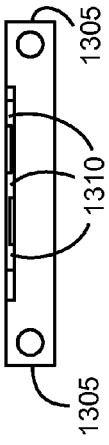
FIG. 13E
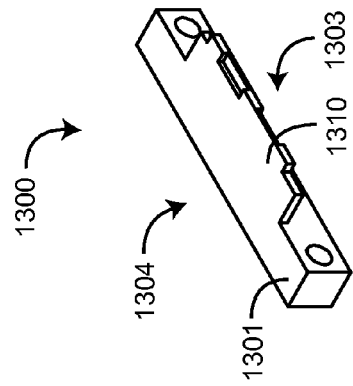
FIG. 13B
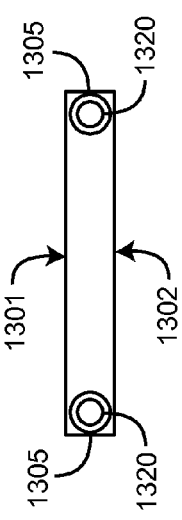
FIG. 13D
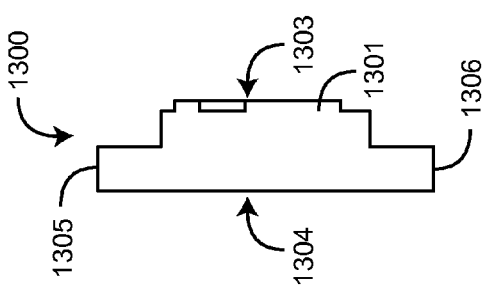
FIG. 13A
FIG. 13C

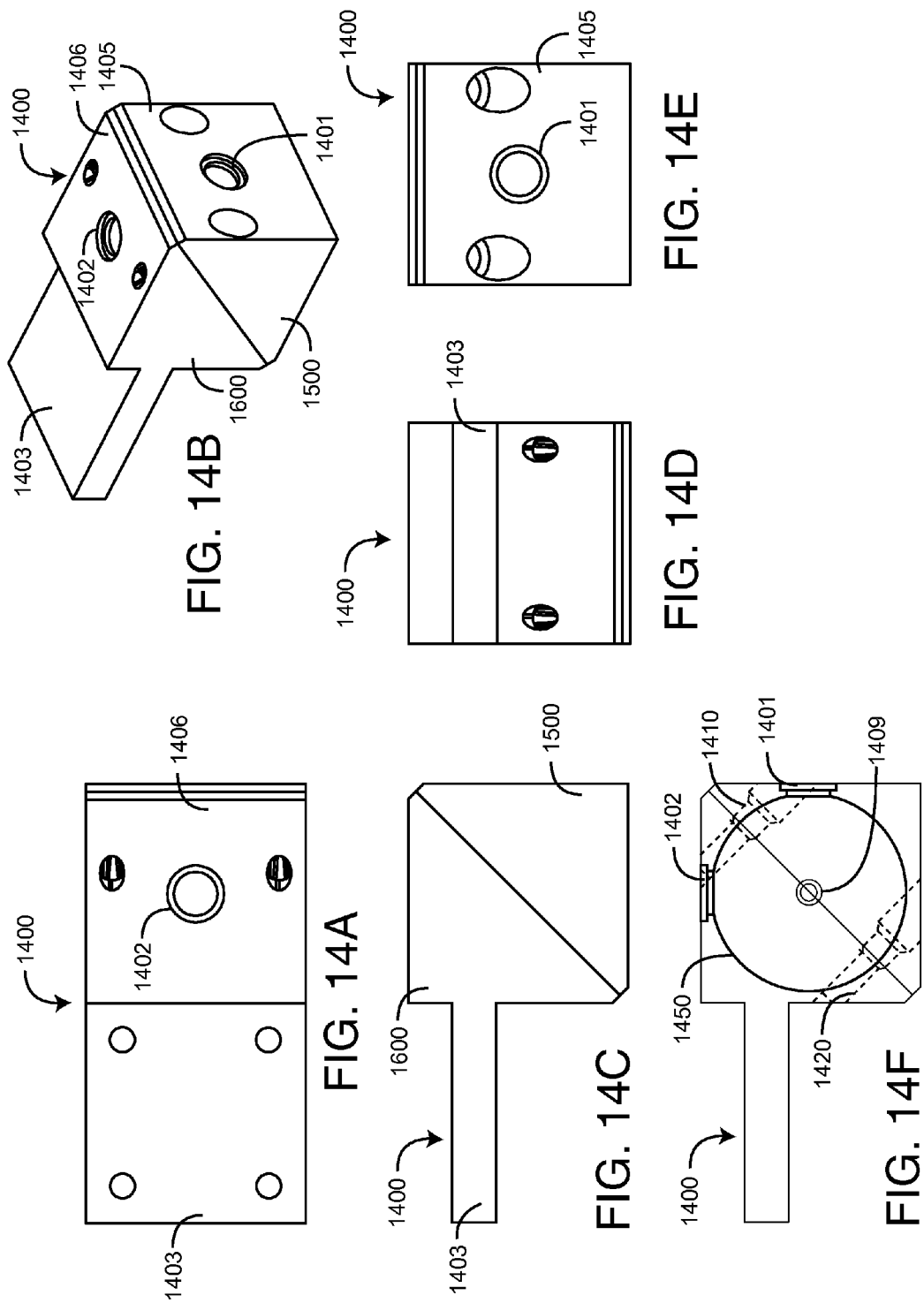

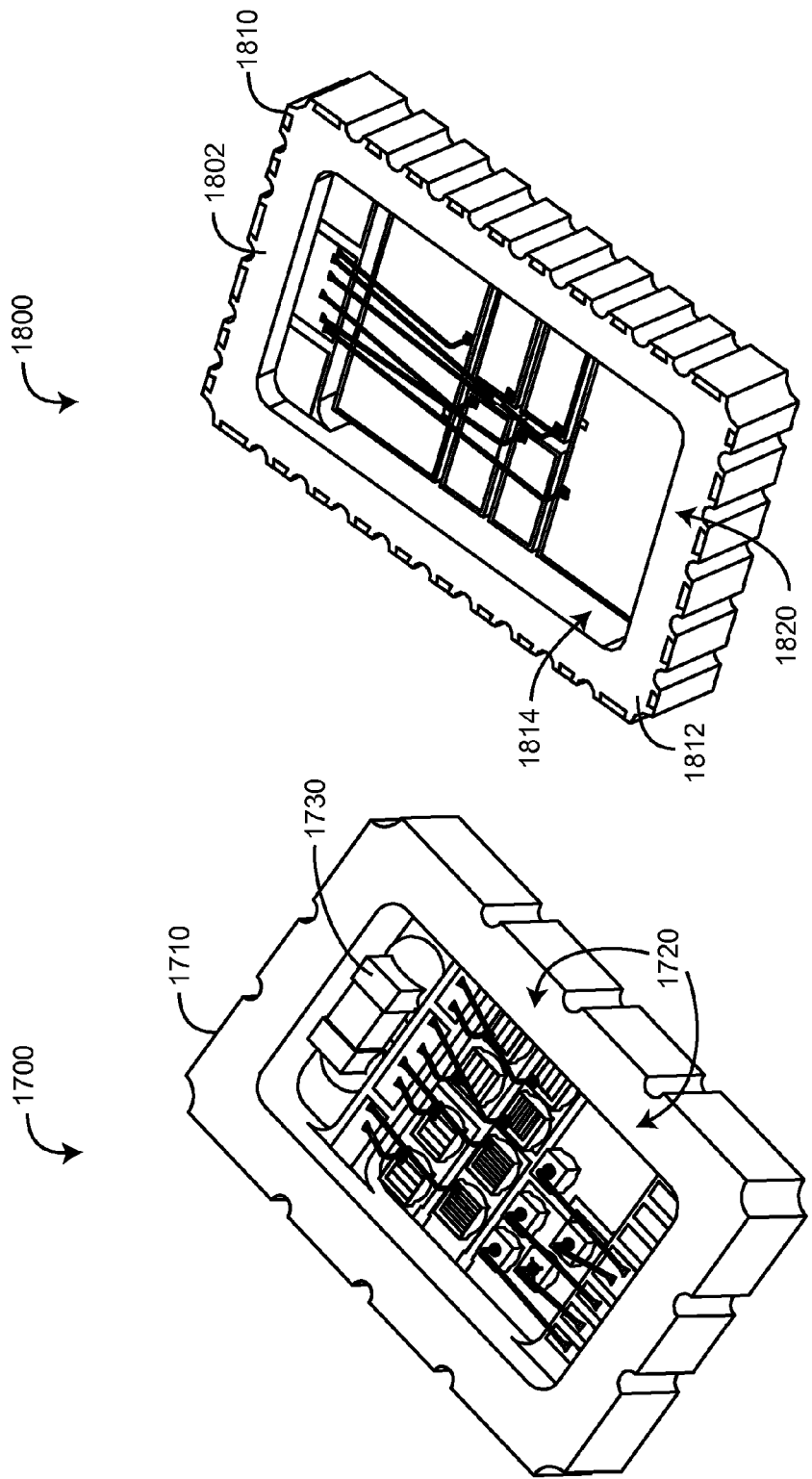

BLOOD ANALYSIS SYSTEM

CROSS-REFERENCE TO RELATED APPLICATIONS

The present application claims priority benefit under 35 U.S.C. §119(e) to U.S. Provisional Patent Application Ser. No. 61/476,512, filed Apr. 18, 2011, titled Blood Analysis System, hereby incorporated in its entirety by reference herein.

BACKGROUND OF THE INVENTION

Noninvasive physiological monitoring systems for measuring constituents of circulating blood have advanced from basic pulse oximeters to monitors capable of measuring abnormal and total hemoglobin among other parameters. A basic pulse oximeter capable of measuring blood oxygen saturation typically includes an optical sensor, a monitor for processing sensor signals and displaying results and a cable electrically interconnecting the sensor and the monitor. A pulse oximetry sensor typically has a red wavelength light emitting diode (LED), an infrared (IR) wavelength LED and a photodiode detector. The LEDs and detector are attached to a patient tissue site, such as a finger. The cable transmits drive signals from the monitor to the LEDs, and the LEDs respond to the drive signals to transmit light into the tissue site. The detector generates a photoplethysmograph signal responsive to the emitted light after attenuation by pulsatile blood flow within the tissue site. The cable transmits the detector signal to the monitor, which processes the signal to provide a numerical readout of oxygen saturation ($SpO_2$) and pulse rate, along with an audible pulse indication of the person's pulse. The photoplethysmograph waveform may also be displayed.

SUMMARY OF THE INVENTION

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated in their entirety by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated in their entirety by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Cercacor Laboratories, Inc., Irvine, Calif. (Cercacor) and all incorporated in their entirety by reference herein. An advanced parameter measurement system that includes acoustic monitoring is described in U.S. Pat. Pub. No. 2010/0274099, filed Dec. 21, 2009, titled Acoustic Sensor Assembly, assigned to Masimo and incorporated in its entirety by reference herein.

Advanced blood parameter measurement systems include Masimo Rainbow® SET, which provides measurements in addition to $SpO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Advanced parameter measurement systems may also include acoustic monitoring such as acoustic respiration rate (RRa™) using a Rainbow Acoustic Sensor™ and Rad-87™ monitor, available from Masimo. Such advanced pulse oximeters, low noise sensors and advanced parameter systems have gained rapid acceptance in a wide variety of medical applications, including surgical wards, intensive care and neonatal units, general wards, home care, physical training, and virtually all types of monitoring scenarios.

A blood analysis system functions as a non-invasive blood parameter analyzer when a monitor is coupled with an optical sensor and as an invasive blood sample analyzer when the monitor is coupled with a blood analysis adapter. The blood analysis adapter has a transmitting assembly and a receiving assembly in electrical communications with the adapter connector so as to receive emitter signals for driving emitters within the transmitting assembly and so as to transmit a detector signal for responding to at least one detector in the receiving assembly. A drawer slidably moves within the receiving assembly so as to extend from the drawer slot in an open position and recede into the drawer slot in a closed position. In the open position, a cuvette pocket in the drawer receives a cuvette containing a blood sample. In the closed position, the blood sample is irradiated with multiple wavelength light from the emitters, the detector responds to the multiple wavelength light after attenuation by the blood sample, and the monitor analyzes the blood sample according to the detector signal.

BRIEF DESCRIPTION OF THE DRAWINGS

FIGS. 1A-B are perspective views of a blood analysis system embodiment having a non-invasive blood parameter monitor (FIG. 1A) configuration and a blood sample analyzer (FIG. 1B) configuration;

FIG. 2A-B illustrate steps for analyzing a blood sample utilizing a blood analysis system including removing a non-invasive sensor (FIG. 2A) and attaching a blood analysis adapter (FIG. 2B);

FIGS. 3A-D further illustrate steps for analyzing a blood sample including taking a blood sample with a cuvette (FIG. 3A); opening a cuvette drawer (FIG. 3B); loading the cuvette into the drawer (FIG. 3C) and closing the drawer so as to position the cuvette inside the blood analysis adapter (FIG. 3D);

FIGS. 4A-E are perspective illustrations of blood sample cuvettes including an un-modulated cuvette (FIG. 4A) embodiment; an angle modulated, tapered cuvette (FIG. 4B) embodiment; a linearly modulated, tapered cuvette (FIG. 4C) embodiment; a volume modulated, flexible cuvette (FIG. 4D) embodiment; and a pressure modulated, flexible cuvette (FIG. 4E) embodiment; respectively, of a blood sample cuvette;

FIGS. 6A-F are top, side, front, perspective, exploded perspective and sample area detail views, respectively, of a blood sample cuvette;

FIGS. 7A-B are an perspective view and an exploded perspective view, respectively, of a blood analysis adapter;

FIGS. 8A-F are top, left, front, right, bottom and perspective views, respectively, of a blood analysis adapter;

FIGS. 9A-B are an exploded perspective views of an optical assembly and an optical assembly optical path, respectively;

FIGS. 10A-B are an exploded perspective view and an elevated end view, respectively, of a drawer assembly;

FIGS. 11A-E are top, perspective, side, back and front views, respectively, of a cuvette drawer;

FIGS. 12A-E are top, perspective, side, back and front views, respectively, of a drawer frame;

FIGS. 13A-E are top, perspective, side, back and front views, respectively, of a spring holder;

FIGS. 14A-F are top, perspective, side, back, front and internal side views, respectively, of an integrating sphere;

FIGS. 17-18 are perspective views of an emitter assembly and a detector assembly, respectively.

DETAILED DESCRIPTION OF THE PREFERRED EMBODIMENTS

Figure 4A:
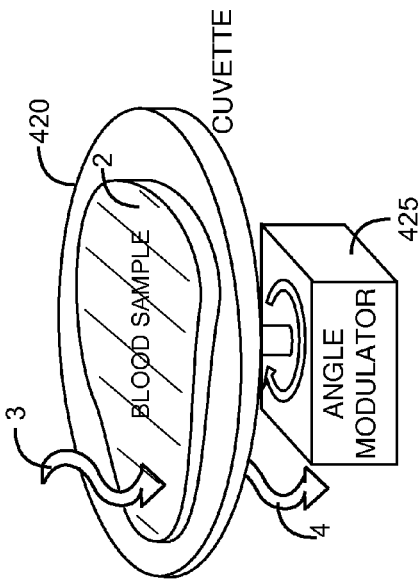

FIGS. 1A-B illustrate a blood analysis system 100 embodiment that advantageously functions as a non-invasive blood parameter analyzer 101 (FIG. 1A) when coupled with an optical sensor 110 or as an invasive blood sample analyzer 102 (FIG. 1B) when coupled with a blood analysis adapter 130. In particular, as a non-invasive blood parameter monitor 101 (FIG. 1A), the blood analysis system 100 has an optical sensor 110 that transmits optical radiation at a multiplicity of wavelengths other than or including the red and infrared wavelengths utilized in pulse oximeters. The blood analysis system 100 also has a monitor 120 that determines the relative concentrations of blood constituents other than or in addition to $HbO_2$ and Hb, such as carboxyhemoglobin (HbCO), methemoglobin (MetHb), fractional oxygen saturation, total hemaglobin (Hbt) and blood glucose to name a few. Further, such a system incorporates other sensors, such as an acoustic sensor, so as to determine other physiological parameters such as respiration rate. A non-invasive blood parameter analyzer is described in U.S. patent application Ser. No. 12/882,111, titled Spot Check Monitor Credit System, filed Sep. 14, 2010 and incorporated in its entirety by reference herein. Also shown in FIGS. 1A-B, as an invasive blood sample analyzer 102 (FIG. 1B), the blood analysis system 100 has a blood analysis adapter 130 that accepts a cuvette 140 containing a blood sample obtained by invasive means, as described in further detailed with respect to FIGS. 2-3, below.

FIG. 2-3 illustrate steps for analyzing a blood sample utilizing a blood analysis system 102 (FIG. 1B). As shown in FIGS. 2A-B, a non-invasive blood parameter analyzer 101 (FIG. 1A) is converted to an invasive blood sample analyzer 102 (FIG. 1B) by removing a noninvasive optical sensor 110 from the monitor 120 (FIG. 2A) and replacing it with a blood analysis adapter 700 (FIG. 2B).

As shown in FIGS. 3A-D, a blood sample 2 is taken with the cuvette 140 (FIG. 3A). In particular, the cuvette 140 is brought into contact with a blood droplet 2 formed by a lancet puncture of a tissue site 1. The blood sample 2 is drawn into the cuvette 140 by capillary action. The cuvette drawer 150 (FIG. 3B) is opened so that it extends from side of the adapter 130 (FIG. 3B). The drawer 150 has cuvette pocket 160 corresponding to cuvette 140. The cuvette 140 containing the blood sample is placed in the drawer 150 (FIG. 3C). The drawer 150 is pushed into the adapter 130 (FIG. 3D). As described with respect to FIGS. 10-11, below, the drawer 150 has push-to-open and push-to-close feature. After the blood sample is analyzed, the drawer 150 is opened and the cuvette 140 is removed and disposed. Another cuvette 140 can be inserted into the drawer 150 for analysis or the drawer 150 can be pushed empty back into the adapter 130. The blood analysis adapter 130 (FIG. 2B) can be removed and an optical sensor 110 (FIG. 2A) re-inserted into the monitor 120 for noninvasive measurements. The blood analysis adapter 130 is described in further detail with respect to FIGS. 7-18, below.

FIGS. 4A-E illustrate blood sample cuvettes for taking an invasive blood sample and analyzing a blood sample utilizing a blood analysis system as described above with respect to FIGS. 1-3. As shown in FIG. 4A, an un-modulated cuvette embodiment 410 is exposed to a blood droplet, such as from a lanced fingertip, so as to obtain a blood sample 2. The blood sample 2 is typically drawn into the cuvette 410 via capillary action. A blood analysis system, as described generally with respect to FIGS. 1-3, above and in further detail with respect to FIGS. 5-18, below, exposes the blood sample 2 to multiple wavelengths of incident optical radiation 3, such as from LEDs. The incident optical radiation 3 is attenuated by the blood sample 2, resulting in emergent optical radiation 4, which is analyzed by a monitor, for example, so as to determine blood parameters corresponding to the blood sample 2, such as hemoglobin and hematocrit, to name just a few.

As shown in FIGS. 4B-E, pulsatile embodiments of a blood sample cuvette extend the advantages of a non-invasive blood parameter monitor, such as a pulse oximeter, to invasive blood sample analysis. In particular, variations in light attenuation of pulsatile blood flow within blood perfused tissue is, ideally, solely dependent on blood constituents. Advantageously, the same principles apply to a pulsatile blood sample cuvette. That is, variations in light attenuation of a "pulsatile" blood sample in a cuvette is, ideally, solely dependent on the blood sample constituents. Further, a pulsatile blood sample cuvette advantageously allows the use of blood analysis algorithms well-developed for use in analyzing pulsatile blood flow in blood perfused tissues.

Figure 4B:
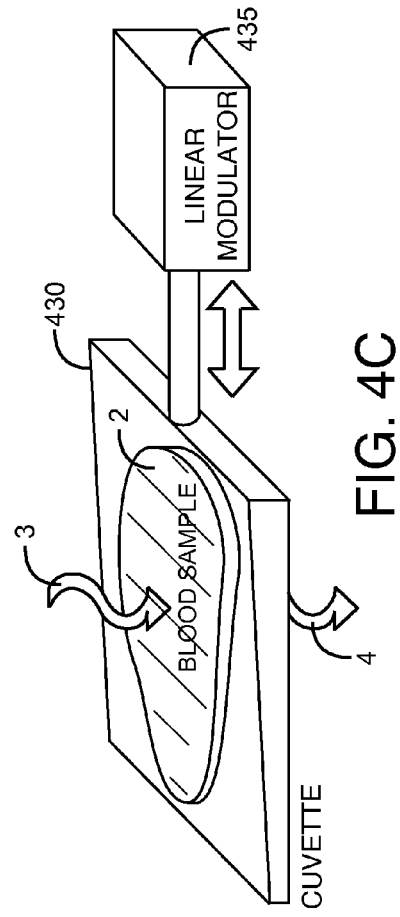
Figure 4C:
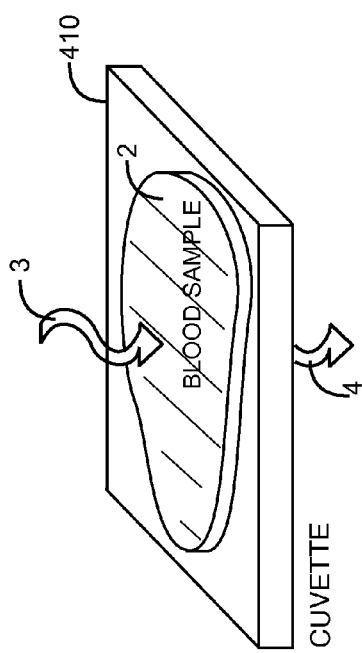

As shown in FIGS. 4B-C, pulsatile blood sample cuvette 420-430 embodiments are advantageously shaped or configured so as to contain and form a tapered blood sample 2 that has a gradual change in thickness from one end of the sample to the other. The tapered blood sample 2 is illuminated with optical radiation 3 and is positionally-modulated so that the thickness of the blood sample exposed to optical radiation 3 varies over time, i.e. is effectively a pulsatile blood sample. Accordingly, the detected optical radiation 4 after attenuation by the thickness-modulated blood sample can be analyzed similarly to a pulsatile blood flow. A pulsatile blood sample cuvette 420-430 has an external opening (not shown) leading to an internal cavity (not shown) configured to draw a blood sample into the cavity via capillary action. In an embodiment, the cuvette is multi-layered as described with respect to FIGS. 6A-E, below. In an embodiment, a pulsatile blood sample cuvette 420-430 forms a tapered blood sample 2 by the cuvette having a tapered shape with a corresponding tapered internal cavity. In other embodiments, the cuvette 420 has a uniform thickness, but the internal cavity is tapered so as to form a tapered blood sample 2.

As shown in FIG. 4B, in an angle modulated embodiment, a pulsatile blood sample cuvette 420 is generally thin and circular for mounting in or on a rotating drawer or platform. An angle modulator 425 has an electric motor for rotating the cuvette 420 across or through various angles so as to expose various portions of the tapered blood sample 2 to optical radiation 3 and so that the detected optical radiation 4 is attenuated by varying thicknesses of the blood sample 2.

As shown in FIG. 4C, in a linear modulated embodiment, a pulsatile blood sample cuvette 430 or its internal cavity is generally wedge-shaped for mounting in or on a translating drawer or platform. A linear modulator 435 has an electric motor for positioning the cuvette 430 back and forth so as to expose various portions of the tapered blood sample 2 to optical radiation 3 and so that the detected optical radiation 4 is attenuated by varying thicknesses of the blood sample 2.

As shown in FIGS. 4D-E, pulsatile blood sample cuvette 440-450 embodiments advantageously have a flexible or flexing cavity 5 so as to form a varying thickness blood sample 2. The blood sample 2 is illuminated with optical radiation 3 and is modulated so that the thickness of the blood sample exposed to optical radiation 3 varies over time, i.e. is a pulsatile blood sample. Accordingly, the detected optical radiation 4 after attenuation by the thickness-modulated blood sample can be analyzed similarly to a pulsatile blood flow. A pulsatile blood sample cuvette 440-450 has an external opening (not shown) leading to an internal cavity (not shown).

As shown in FIG. 4D, in a volume modulated embodiment 440, a pulsatile blood sample cuvette 440 has a generally flexible cavity having a generally reduced volume state 442 and a generally increase volume state 444. A volume modulator 445 increases and decreases the cavity volume so as to expose a varying thickness portion of the blood sample to optical radiation 3 and so that the detected optical radiation 4 is attenuated by a varying blood sample 2 thickness accordingly. In an embodiment, the volume modulator 445 varies the volume of blood in the flexible cavity 5 by alternately removing 442 or adding 444 a gas, liquid or solid into the flexible cavity so as to partially expand and contract the blood volume, decreasing and increasing its thickness accordingly. In an embodiment, removes or adds to the flexible cavity portions of the blood sample itself.

As shown in FIG. 4E, in a pressure modulated embodiment, a pulsatile blood sample cuvette 450 has a generally flexible cavity having a generally reduced volume state 452 and a generally increase volume state 454. A pressure modulator 455 increases and decreases the cavity volume so as to expose a varying thickness portion of the blood sample to optical radiation 3 and so that the detected optical radiation 4 is attenuated by a varying blood sample 2 thickness accordingly. In an embodiment, the pressure modulator 455 varies the volume of blood in the flexible cavity 5 by alternately squeezing 452 or pulling 454 or releasing the flexible cavity so as to partially expand and contract the blood volume within, decreasing and increasing its thickness accordingly. In various embodiments, the pressure modulator 455 is a mechanical device, such as solenoid activate plunger or an electrically actuate caliper. In other embodiments, the pressure modulator 455 is a gas surrounding the flexible cuvette that is regulated so as to have increasing or decreasing pressure.

Figure 5A:
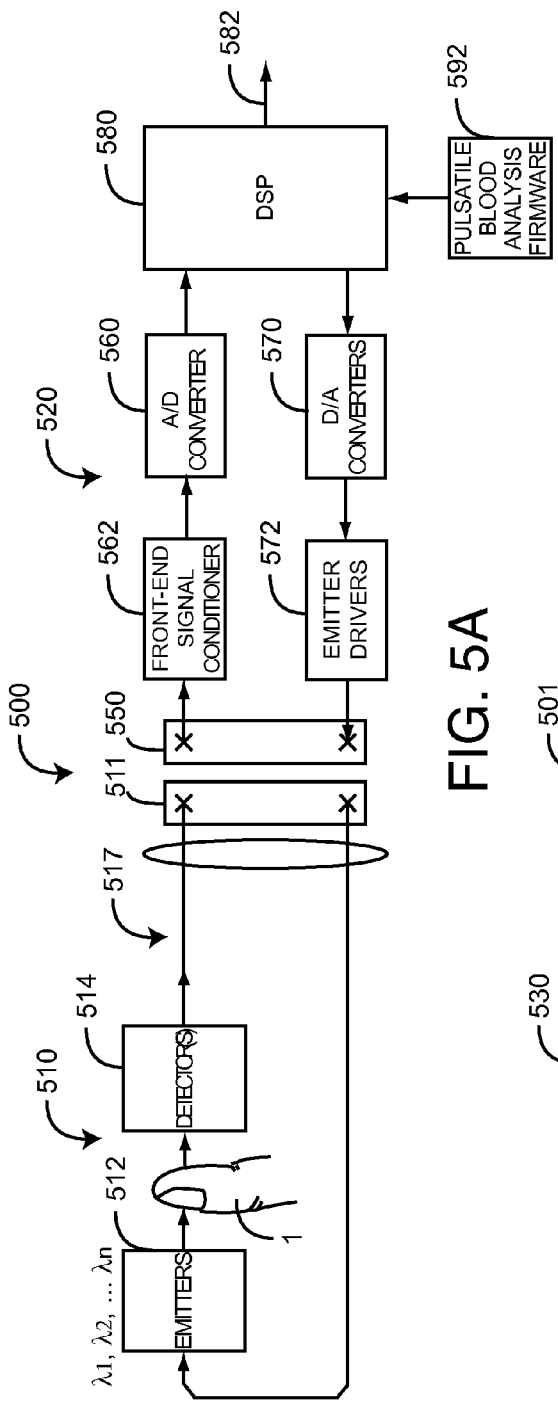
FIGS. 5A-C are block diagrams of a blood analysis system embodiment for a non-invasive blood parameter monitor (FIG. 5A) configuration; a blood sample analyzer (FIG. 5B) configuration; and a pulsatile blood sample analyzer (FIG. 5C) configuration.
Figure 5B:
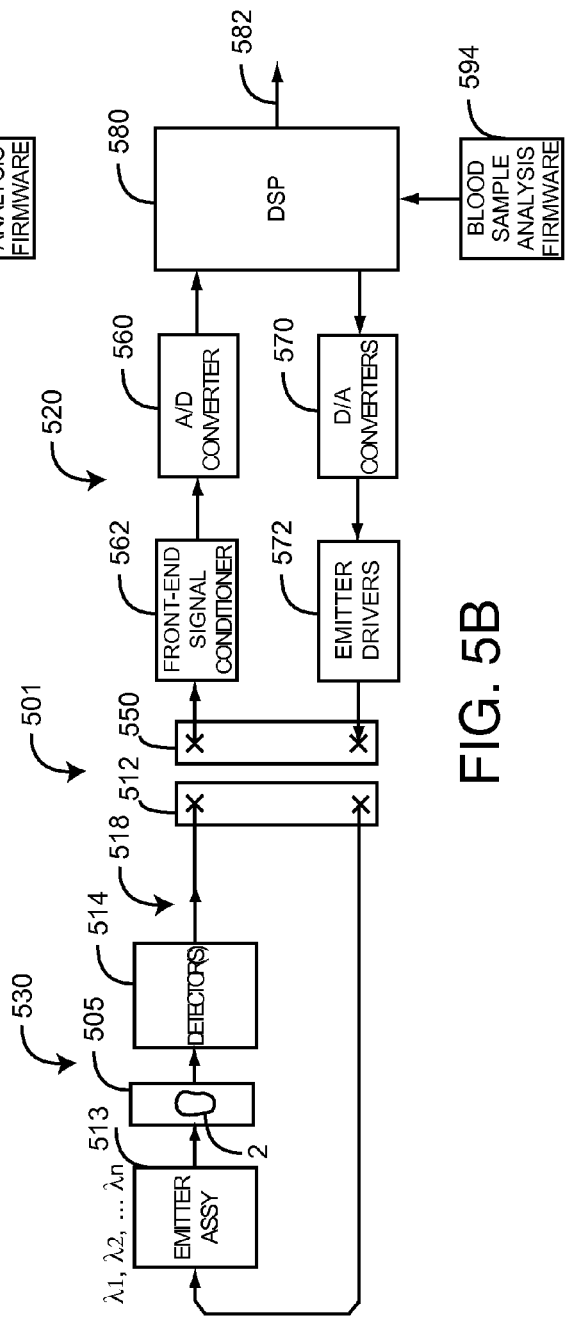
Figure 5C:
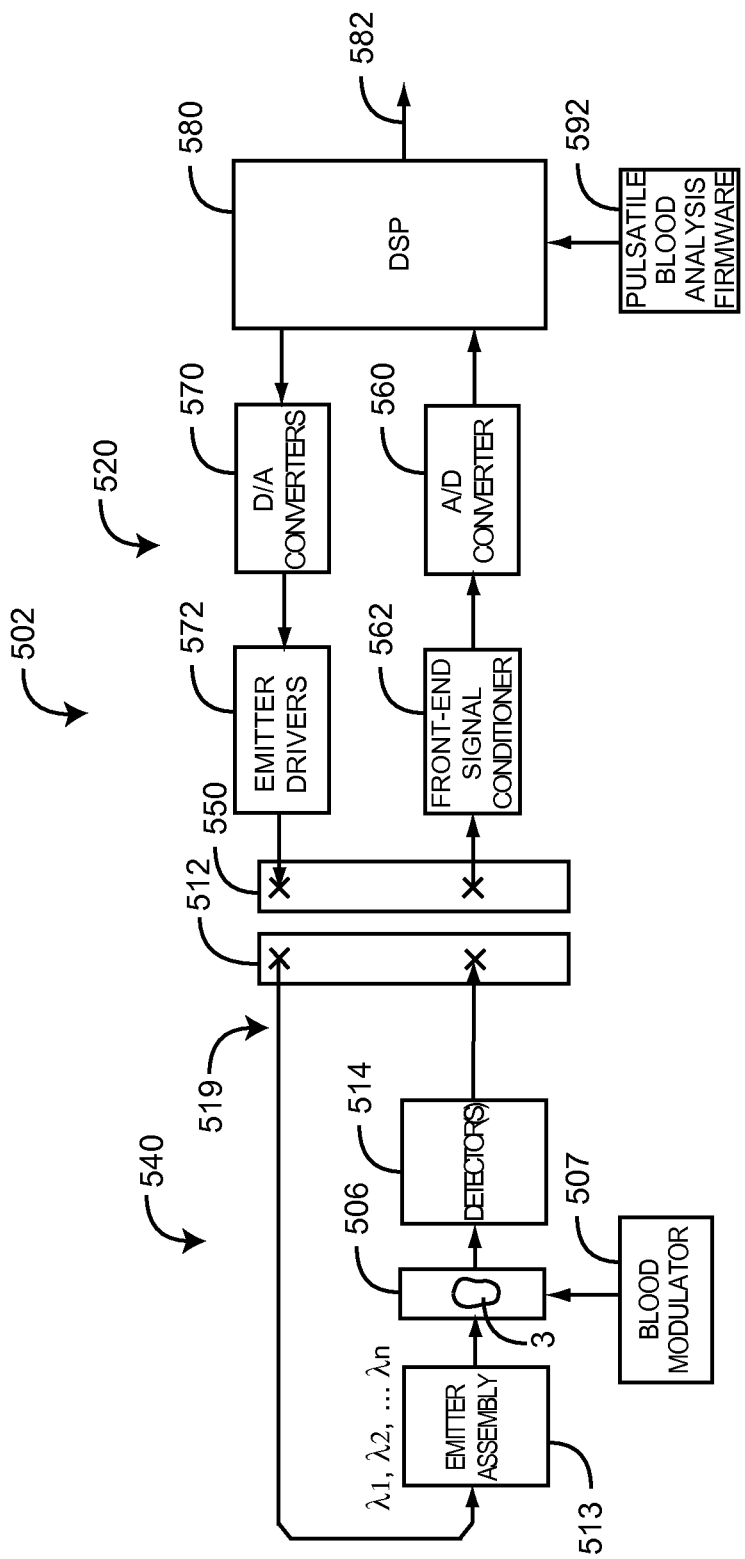
Figure 15B:
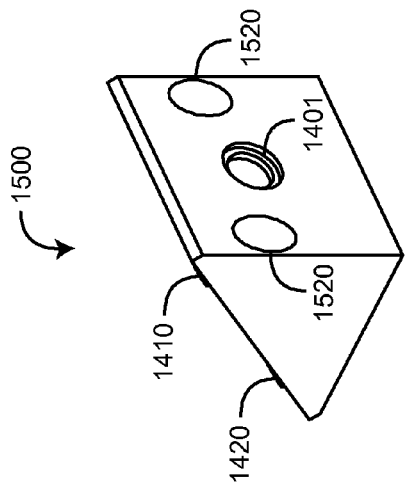
FIGS. 15A-E are top, perspective, side, front and back views, respectively, of an integrating sphere front-half.
Figure 15E:
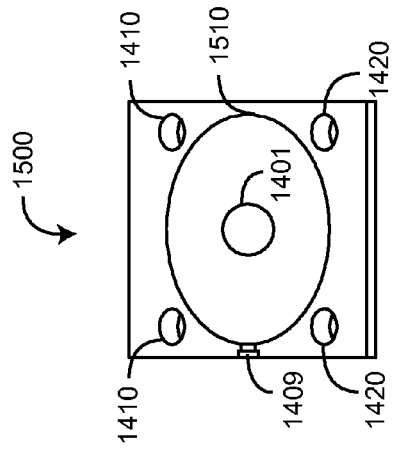
Figure 15D:
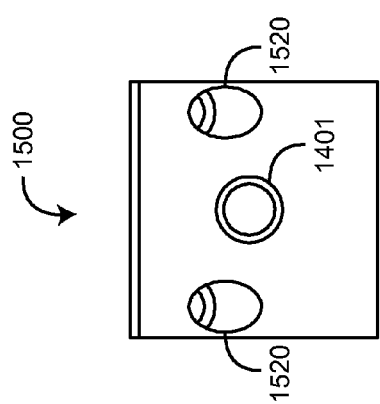
Figure 15A:
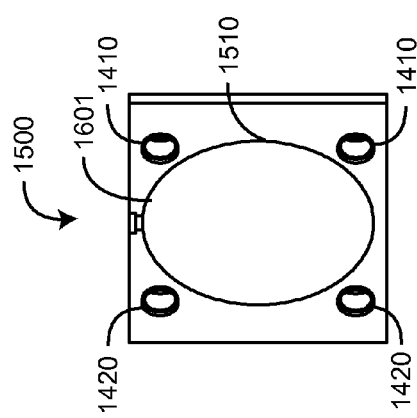
Figure 15C:
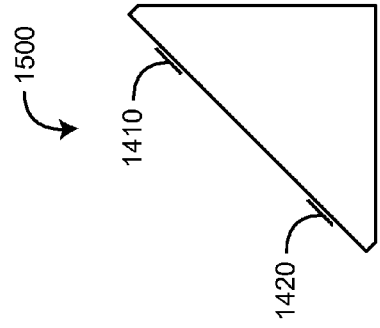
Figure 16B:
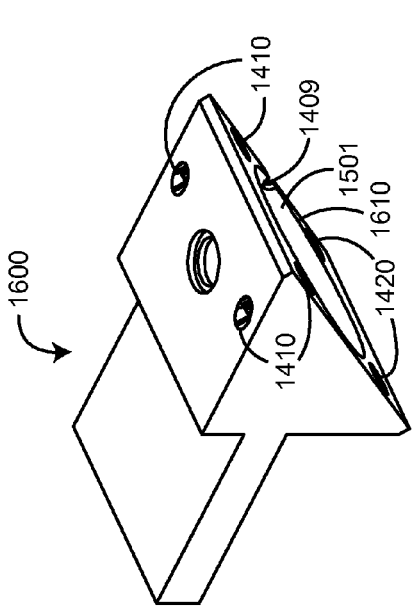
FIGS. 16A-E are top, perspective, side, back and front views, respectively, of an integrating sphere back-half.
Figure 16E:
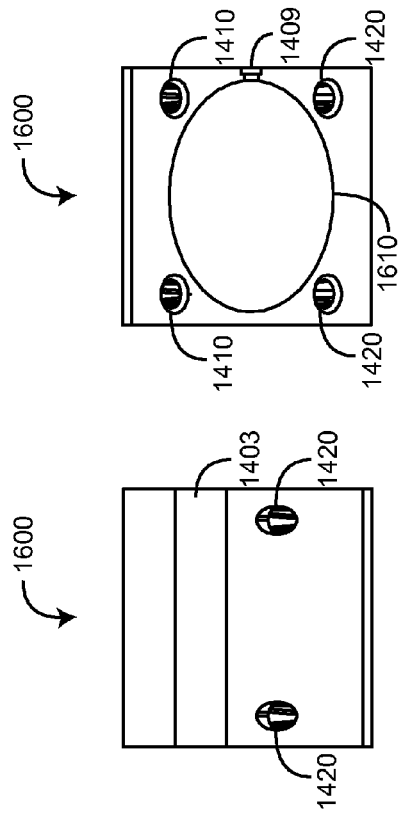
Figure 16D:
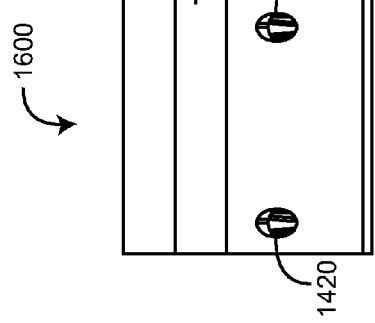
Figure 16A:
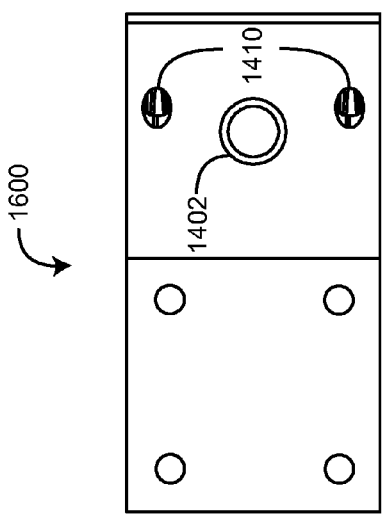
Figure 16C:
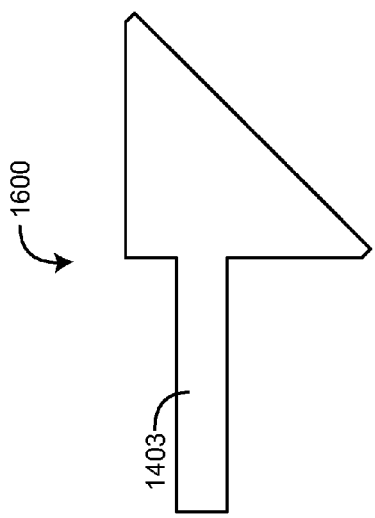

FIGS. 5A-C illustrate blood analysis system embodiments that include a non-invasive blood parameter analyzer 500 (FIG. 5A) configuration, a blood sample analyzer 501 (FIG. 5B) configuration, and a pulsatile blood sample analyzer 502 (FIG. 5C) configuration. As shown in FIG. 5A, the blood parameter analyzer 500 has an optical sensor 510 that connects with a monitor 520 via a sensor cable 517. The optical sensor 510 includes multiple-wavelength emitters 512 and one or more detectors 514 in communications with a sensor connector 511 via the sensor cable 517. The sensor connector 511 mates with a corresponding monitor connector 550. The monitor 520 has D/A converters 570 and corresponding emitter drivers 572 that selectively activate the emitters 512 so as to illuminate a tissue site 1. The detector(s) 514 is responsive to the emitted light after attenuation by pulsatile blood flow within the tissue site 1. The monitor 520 also has an ND converter 560 and a corresponding front-end signal conditioner 562 responsive to the detector 514. A digital signal processor (DSP) 580 drives the D/A converters 570 so as to activate the emitters 512 and receives the detector 514 response via the ND converter 560. Pulsatile blood analysis firmware 592 analyzes the detector signal and generates corresponding physiological parameters among other processor outputs 582 that can be shown on a monitor display 122 (FIGS. 1A-B) or communicated to one or more external devices via monitor input/output ports 124 (FIGS. 1A-B).

As shown in FIG. 5B, the blood sample analyzer 501 has an optical adapter 530 that connects with the monitor 520 interchangeably with optical sensor 510 (FIG. 5A). The optical adapter 530 includes a multiple-wavelength emitter assembly 513 and one or more detectors 514 in communications with an adapter connector 512 via an internal (or external) adapter cable 518. The adapter connector 512 mates with a corresponding monitor connector 550. The monitor 520 has D/A converters 570 and corresponding emitter drivers 572 that selectively activate the emitters of the emitter assembly 513 so as to illuminate the blood sample 2 within a cuvette 505. In an embodiment, the emitter assembly 513 includes an integrating sphere 1400 (FIGS. 14A-F) that advantageously provides uniform illumination of the blood sample, as described with respect to FIGS. 9A-B, below. The detector(s) 514 is responsive to the emitted light after attenuation by the blood sample 2. The monitor 520 also has an ND converter 560 and a corresponding front-end signal conditioner 562 responsive to the detector 514. A digital signal processor (DSP) 580 drives the D/A converters 570 so as to activate the emitter assembly 513 and receive the detector 514 response via the ND converter 560. Blood sample analysis firmware 594 analyzes the detector signal and generates corresponding physiological parameters among other processor outputs 582 that can be shown on the monitor display 122 (FIGS. 1A-B) or communicated to one or more external devices via monitor input/output ports 124 (FIGS. 1A-B).

As shown in FIG. 5C, the pulsatile blood sample analyzer 502 has an optical adapter 540 that connects with monitor 520 interchangeably with an optical sensor 510 (FIG. 5A). The optical adapter 540 includes a multiple-wavelength emitter assembly 513 and one or more detectors 514 in communications with an adapter connector 512 via an internal (or external) adapter cable 519. The adapter connector 512 mates with a corresponding monitor connector 550. The monitor 520 has D/A converters 570 and corresponding emitter drivers 572 that selectively activate the emitters within the emitter assembly 513 so as to illuminate a blood sample 3 within a pusatile cuvette 506. In an embodiment, the emitter assembly 513 includes an integrating sphere that advantageously provides uniform illumination of the blood sample, as described with respect to FIGS. 9A-B, below. The detector(s) 514 is responsive to the emitted light after attenuation by the blood sample 3. The monitor 520 also has an ND converter 560 and a corresponding front-end signal conditioner 562 responsive to the detector 514. A digital signal processor (DSP) 580 drives the D/A converters 570 so as to activate the emitter assembly 513 and receives the detector 514 response via the ND converter 560.

Further shown in FIG. 5C, the optical adapter 540 has a blood modulator 507 that advantageously modulates the pulsatile cuvette 506 and/or the blood sample 3 so as to cause the blood sample 3 to appear pulsatile to the emitter assembly 513 and detector(s) 514, as described with respect to FIGS. 4A-E, above. The monitor 520 has pulsatile blood analysis firmware 592 that analyzes the corresponding detector 514 signal so as to generate corresponding physiological parameters among other processor outputs 582 that can be shown on the monitor display 122 (FIGS. 1A-B) or communicated to one or more external devices via monitor input/output ports 124 (FIGS. 1A-B).

FIGS. 6A-F illustrate a blood sample cuvette 600 having a curved front end 601, a blood sample cavity 602 and a back end 603. The cuvette 600 further has a center layer 620 disposed between a first outside layer 610 and a second outside layer 630. In various embodiments, the outside layers 610, 630 are glass, plastic or other materials of uniform thickness. In an embodiment, the outside layers 610, 630 are transparent between about 850-2500 nm. The outside layers 610, 630 are separated and bonded by the center layer 620. In an embodiment, the center layer 620 is opaque. In an embodiment, the center layer 620 has a shaped end 622 recessed from the curved front ends 601 of the outside layers 610, 630.

As shown in FIG. 6F, the blood sample cavity 602 (FIG. 6D) defines a blood sample volume 650. In particular, the blood sample surface area 655 is bounded by the curved end 501 of the outside layers and the shaped end 622 of the center layer 620. The blood sample thickness 656, or optical pathlength, is bounded by the gap between the outside layers 610, 630, which is defined by the center layer thickness 623 (FIG. 6E). In an embodiment, the center layer is a double sided tape having a 0.1-0.2 mm thickness. In an embodiment, the cuvette layers 610, 620, 630 and corresponding cavity 602 are sized so that the blood sample volume 650 ranges from about 0.5-5 μL.

FIGS. 7-8 illustrate a blood analysis adapter 700 generally described with respect to FIGS. 1-5, above. The blood analysis adapter 700 has an adapter body 701, an adapter connector 710 and a drawer slot 720 (FIG. 7A). The adapter body 701 has a bottom piece 702 and a top piece 703 housing an optical assembly 900 (FIG. 7B). The adapter connector 710 extends from the bottom piece 702. The drawer slot 720 is defined in a body side 705. The optical assembly 900 has a transmitting assembly 910, a circuit board 920 and a receiving assembly 930, described in detail with respect to FIGS. 9A-B, below. The optical assembly 900 is disposed within the body 701 so that a receiving assembly 930 is proximate the side 705 and a drawer 1100 (FIGS. 9A-B) is proximate the drawer slot 720 so as to movably extend through and retract from the drawer slot 720. The adapter connector 710 mates with a corresponding monitor connector 550 (FIG. 5B). A connector cable 712 removably mates with a corresponding circuit board connector 929 so as to provide electrical communications between the optical assembly 900 and the adapter connector 710. In other embodiments, the connector 710 is mounted directly to the circuit board 920 or the circuit board 920 is otherwise directly connected mechanically and electrically to the connector 710. The optical assembly 900 provides an electrical interface to a monitor 120 (FIG. 1B) via the adapter connector 710, connector cable 712 and circuit board connector 929. Accordingly, the monitor 120 (FIG. 1B) activates emitters (FIG. 17) in the transmitting assembly 910, which illuminate a blood sample 650 (FIG. 6F) within a cuvette 600 (FIGS. 6A-E) disposed within the drawer 1100 (FIGS. 9A-B); and a detector or detectors (FIG. 18) within the receiving assembly 930 detect the emitted optical radiation after attenuation by the blood sample 650 (FIG. 6F) and output the result to the monitor 120 (FIG. 1B) for processing and analysis.

FIGS. 9A-B illustrate an optical assembly 900 having a transmitting assembly 910, a circuit board 920 and a receiving assembly 930. As shown in FIG. 9A, the transmitting assembly 910 has an integrating sphere 1400 and an emitter assembly 912. The receiving assembly 930 has a drawer assembly 1000 and a detector assembly 932. The transmitting assembly 910 is disposed on a first side 921 of the circuit board 920 and mechanically attached to the board 920 via fasteners (not shown) extending through an integrating sphere mount 1403 and secured to the board 920 so that an integrating sphere output face 1406 extends through a circuit board aperture 925. The transmitting assembly 910 is electrically connected to the board 920 via first board contacts (not shown) disposed on the circuit board 920; emitter assembly contacts (not shown) disposed on the emitter assembly 912; and an interconnect (not shown) extending between the first board contacts and the emitter assembly contacts. The first board contacts, in turn, are in electrical communications with a board connector 929 (FIG. 7B), which attaches a connector cable 712 (FIG. 7B) so as to conduct signals from the emitter drivers 572 (FIG. 5B) in the monitor 120 (FIG. 1B) to the emitters 1700 (FIG. 9B). In an embodiment, the interconnect is a ribbon cable terminated at both ends with an insulation-displacement connector (IDC); and the first board contacts and the emitter assembly contacts are board edge or pin-type contacts.

Also shown in FIG. 9A, the receiving assembly 930 is disposed on a second side 922 of the circuit board 920 and mechanically attached to the board 920 via fasteners (not shown) extending through drawer assembly mounts 1220 and secured to the board 920 so that drawer assembly apertures 1110, 1210 (FIG. 9B) are generally centered over the board aperture 925 and generally aligned with an integrating sphere output aperture 1402. The receiving assembly 930 is electrically connected to the board 920 via second board contacts (not shown) disposed on the circuit board 920; detector assembly contacts (not shown) disposed on the detector assembly 932; and an interconnect (not shown) extending between the second board contacts and the detector assembly contacts. The second board contacts (not shown), in turn, are in electrical communications with a board connector 929 (FIG. 7B), which attaches a connector cable 712 (FIG. 7B) so as to conduct signals from the detector(s) 1800 (FIG. 9B) to the front-end 562 (FIG. 5B) in the monitor 120 (FIG. 1B). In an embodiment, the interconnect is a ribbon cable terminated at both ends with an IDC connector; and the second board contacts and the detector assembly contacts are board edge or pin-type contacts.

As shown in FIG. 9B, the emitter assembly 912 has an emitter housing 940, an emitter 1700 and emitter optics 950. The emitter housing 940 mounts the emitter 1700 and electrically connects emitter contacts (not shown) to the emitter assembly contacts (not shown). The emitter housing 940 also mounts the emitter optics 950, which may include one or more of an emitter lens, a diffuser or a spacer that function to optically couple multiple wavelength light from the emitter 1700 into the integrating sphere input aperture 1401. In various embodiments, the emitter housing 940 may be a printed circuit board or a ceramic chip carrier, to name a few.

Further shown in FIG. 9B, the detector assembly 932 has a detector housing 950, a detector 1800 and detector optics 970. The detector housing 950 mounts the detector 1800 and electrically connects detector contacts (not shown) to the detector assembly contacts (not shown). The detector housing 950 also mounts the detector optics 970, which may include one or more of a detector lens, a diffuser or a spacer that function to optically couple multiple wavelength light from the integrating sphere output aperture 1402 to the detector 1800. In various embodiments, the detector housing 950 may be a printed circuit board or a ceramic chip carrier, to name a few.

Also shown in FIG. 9B, an optical path 901 originates from the emitter 1700 and terminates at the detector 1800. From the emitter 1700, the optical path traverses the emitter optics 950 to the integrating sphere input aperture 1401 and exits the integrating sphere 1400 output aperture 1402. The integrating sphere 1400 advantageously combines the light transmitted from multiple LEDs having multiple wavelengths so that a blood sample in the cuvette has spatially uniform illumination for all wavelengths.

Further shown in FIG. 9B, from the integrating sphere 1400, the optical path 901 extends through the board aperture 925, through a drawer aperture 1110 and into a blood sample 655 (FIG. 6F) disposed within a cuvette aperture 602 of the cuvette 600. The drawer 1100 has an open position that receives the cuvette 600 and a closed position the inserts the cuvette 600 into the drawer frame 1200. Advantageously, in the closed position, the drawer 1100 accurately positions a blood sample within the cuvette aperture 602 over the optical path 901 and protects the blood sample from contamination. The optical path 901 exits the cuvette aperture 602 and extends through the drawer frame aperture 1210, through the detector optics 970 and terminates at the detector 1800. The drawer assembly 1000 including the drawer 1100 and drawer frame 1200 is described in detail with respect to FIGS. 10-13, below. The integrating sphere 1400 is described in detail with respect to FIGS. 14-16, below. The emitter 1700 and detector 1800 are described with respect to FIGS. 17-18, below.

FIGS. 10A-B illustrate a drawer assembly 1000 having a drawer 1100, a drawer frame 1200, a spring 1010 and a spring retainer 1300. The drawer 1100 is retained within the drawer frame 1200 and has an open position FIGS. 4A-B and a closed position FIG. 4C. In the open position, the drawer 1100 has an exposed cuvette pocket 1120, which removably retains a cuvette 600 (FIGS. 6A-E). In the closed position, the drawer 1100 positions a cuvette such that the cuvette aperture 602 (FIG. 6D) and a drawer aperture 1122 are in alignment with an optical path 901 (FIG. 9B) so that a blood sample can be optically analyzed, as described with respect to FIGS. 1-4, above.

As shown in FIGS. 10A-B and 11A-E, the drawer 1100 has an upper surface 1111, a lower surface 1112, a front face 1113, a back face 1114 and side rails 1115. The cuvette pocket 1120 is defined by and disposed within the drawer 1100 between the upper surface 1111 and a pocket floor 1121. The drawer aperture 1122 is defined in the pocket floor 1121 so as to provide a through-hole in the drawer 1100 between the upper and lower surfaces 1111, 1112. A finger aperture 1124 is defined in the pocket floor 1121 so as to provide a through-hole in the drawer 1100 between the upper and lower surfaces 1111, 1112 that allows a person to easily remove a cuvette from the drawer 1100.

Also shown in FIGS. 10A-B, 11A-E and 12A-E, the drawer side rails 1115 insert into drawer frame slots 1215 so as to slidably mount the drawer 1100 within the drawer frame 1200. The drawer front face 1113 is finger-pressed to close and lock the drawer 1100 within the frame 1200 and finger-pressed again to unlock and open the drawer 1100 from the frame 1200. A spring slot 1130 is defined by and disposed within the drawer 1100 proximate the back face 1114. The spring slot 1130 defines a spring path 1132 that captures a spring end 1012 (FIGS. 10A-B). In particular, the spring path 1132 is W-shaped so as to lock the drawer 1100 within the frame 1200 upon a first finger press and unlock the drawer from the frame 1200 upon a second finger press as the spring end 1012 (FIGS. 10A-B) travels along the spring path 1132. The drawer 1100 is easily removed from the drawer frame for cleaning by disengaging the spring end 1012 from the spring slot 1130.

Further shown in FIGS. 10A-B and 12A-E, the drawer frame 1200 has a top side 1211, a bottom side 1212, a right side 1218, a left side 1219, a front side 1213 and a back side 1214. A frame aperture 1210 provides a through-hole between the top and bottom sides 1211, 1212. The drawer frame slots 1215 are defined on the drawer bottom side 1212 so as to extend along the left and right sides 1218, 1219 from the front 1213 to the back 1214. The back side 1214 has spring mounts 1230 that removably retain the spring 1010 (FIGS. 10A-B) and a spring slot 1240 that accommodates the spring end 1012 (FIGS. 10A-B). The back side 1214 also has fastener holes 1240 that accommodate screws, bolts, rivets or similar fasteners for attaching the spring retainer 1300 (FIGS. 13A-E) to the drawer frame 1200. The drawer frame 1200 has mount holes 1220 defined within corresponding mount ears 1222 that accommodate screws, bolts, rivets or similar fasteners for mounting the drawer frame 1200 to the circuit board 920 (FIGS. 9A-B).

Also shown in FIGS. 10A-B and 13A-E, the spring retainer 1300 has a top side 1301, a bottom side 1302, a front side 1303, a back side 1304, a right side 1305 and a left side 1306. The right and left sides 1305, 1306 each have fastener thru-holes 1320 that accommodate screws, bolts, rivets or similar fasteners for attaching the spring retainer 1300 to the drawer frame 1200 so as to retain the spring 1010 (FIGS. 10A-B) in place along the drawer frame back side 1214 (FIG. 10B). In particular, the spring retainer 1300 has spring mounts 1310 that mesh with corresponding drawer frame spring mounts 1230 so as to partially encase the spring 1010 and hold it in position.

FIGS. 14-16 illustrate an integrating sphere 1400, which is a portion of the optical assembly 900 (FIGS. 9A-B) described above. In particular, the integrating sphere mounts an emitter assembly 912 (FIGS. 9A-B) and is mounted to a circuit board 920 (FIGS. 9A-B) so as to illuminate a blood sample. The optical assembly has an entrance aperture 1401 that receives light from LEDs 1720 (FIG. 17) and that advantageously transmits light from an exit aperture 1402 having a spatially uniform intensity as a function of wavelength. This spatial uniformity is achieved, at least in part, by a reflective spherical cavity 1401, which mixes the multiple wavelengths of LED light via multiple reflections within the cavity 1401.

As shown in FIGS. 14-16, the integrating sphere 1400 has lower half 1500 and an upper half 1600. Combined, the halves 1500, 1600 define the spherical cavity 1450 (FIG. 14F). The halves 1500, 1600 are held together by fasteners (not shown) threaded or otherwise disposed through upper 1410 and lower 1420 thru-holes. The integrating sphere halves 1500, 1600 also define an input aperture 1401, an output aperture 1402 and a cavity access hole 1409 (FIG. 14F).

FIG. 17 illustrates an emitter 1700 having a substrate 1710 containing multiple layers of bonding pads, traces, feed-thrus and solder pads so as to mount and interconnect multiple LEDs 1720 in an array. In an embodiment, the emitter 1700 has multiple LEDs in the wavelength range of 850-2600 nm for absorption measurements, such as InGaAs, extended InGaAs and germanimum devices to name a few. In an embodiment, the substrate 1710 also contains a thermistor 1730, the resistance of which can be measured in order to determine the bulk temperature of the LEDs 1720 so as to more accurately characterize the LEDs, such as emitted intensity versus wavelength properties. The thermal characteristics of ceramic substrate stabilize and normalize the bulk temperature so that the thermistor measurement of bulk temperature is meaningful.

FIG. 18 illustrates a detector 1800 having a ceramic substrate 1810 that mounts one or more photodiodes 1820. The ceramic substrate 1810 has a body 1812 defining a cavity 1814. The cavity 1814 contains bonding pads that mount the photodiode(s) 1820 and electrically connect the photodiode(s) 1820, if more than one, in parallel. In an embodiment, a single Si photodiode 1820 is utilized. In an embodiment, multiple photodiodes utilize parallel connected combinations of one or more Si photodiodes and one or more InGaAs photodiodes. The Si photodiodes are generally responsive to red and shorter near-IR wavelengths. The InGaAs photodiodes are generally responsive to longer near-IR wavelengths. In an embodiment, a thermistor is also attached to the detector ceramic in order to determine detector temperature to compensate for photodiode drift. An emitter and a detector are described with to U.S. patent application Ser. No. 12/056,179 filed Mar. 26, 2008 titled Multiple Wavelength Optical Sensor, assigned to Masimo Laboratories, Inc., Irvine, Calif. and incorporated by reference herein.

In various embodiments, a cuvette 600 (FIGS. 6A-E) may have a built-in lancet. The lancet may be disposed on the opposite side of the cuvette cavity 602. In that embodiment, the user lances the skin then turns the strip to collect the blood. In an embodiment, the lancet is disposed on the same side as the cuvette cavity so as to allow users to lance and fill the cavity with blood without moving the cuvette. or to move the cuvette over slightly to collect the blood. In an embodiment, the cuvette is constructed of an optically encoded material having a signature that can be detected by wavelengths used during measurement so as to identify the cuvette type. In an embodiment, the cuvette contains a small molecule metabolite reporter (SMMR) that binds with glucose or other blood constitutes in blood and produces a fluorescent signal proportional to the glucose concentration in the sample. In an embodiment, the cuvette material may selectively attenuate high power SLEDs in the 1400-1800 nm range. In an embodiment, a glass cuvette material may be transparent in the 3000-12000 nm range to use with a temperature or heat sensing detector. In an embodiment, the cuvette transmission characteristics is measured and known in advance.

In an embodiment, the cuvette 600 (FIGS. 6A-E) carries a barcode or memory chip that is read during insertion of the cuvette into the blood analysis adapter 700 (FIGS. 7-8). In particular, a drawer 1100 or drawer frame 1200 embodiment contains a bar code or memory reader. The barcode may be used for security or for identification of a cuvette lot, expiration date or blood component type, to name a few.

In an embodiment, a blood analysis adapter 700 (FIGS. 7-8) is loaded with disposable lancets, which can be deployed from the adapter for ease of use. In an embodiment, the adapter 700 is mounted with a gyroscope and/or accelerometer to ensure a preferable position/condition of adapter during use, i.e. to negate gravity effects on a blood sample in the cuvette.

In an embodiment, the cuvette cavity 602 may contain cell lysing chemicals such as sodium dicholate or saponin. Chemicals may be added to the cuvette, such as sodium nitrite and sodium azide, for conversion of the hemoglobin to methemoglobin and azidemethemoglobin. In an embodiment, the cavity design restricts cell membranes from entering the photon path after the red blood cells have been lysed in order to reduce scattering and have a more uniform sample.

In various emitter 1700 (FIG. 17) and detector 1800 (FIG. 18) embodiments, a thermistor is positioned to read the cuvette and blood sample temperature. In an embodiment, the detector contains multiple independent detection channels.

In an embodiment, the emitter 1700 further comprises LEDs in the 250-450 nm wavelength range so as to excite an SMMR molecule or a natural fluorescing molecule in the sample. In an embodiment, the emitter 1700 also contains photodiodes in the 3000-12000 nm range in order to determine the temperature of the cuvette or the sample inside the cuvette.

A blood analysis system has been disclosed in detail in connection with various embodiments. These embodiments are disclosed by way of examples only and are not to limit the scope of the claims that follow. One of ordinary skill in art will appreciate many variations and modifications.

What is claimed is:

1. A blood analysis system functions as a non-invasive blood parameter analyzer when a monitor is coupled with an optical sensor and as an invasive blood sample analyzer when the monitor is coupled with a blood analysis adapter, the blood analysis system comprising:
    a monitor having a sensor port and emitter drivers;
    the emitter drivers are in communications with a sensor port;
    a blood analysis adapter is removably connected to the sensor port;
    the blood analysis adapter has an emitter assembly and a detector;
    the emitter assembly transmits multiple wavelength optical radiation to a blood sample inserted into the blood analysis adapter in response to the emitter drivers;
    a blood modulator that modulates the blood sample so as to simulate pulsatile blood;
    the detector is responsive to the optical radiation after attenuation by the blood sample; and
    the detector response is communicated to the monitor for analysis of the blood sample.

2. The blood analysis system according to claim 1 wherein the blood sample is tapered.

3. The blood analysis system according to claim 2 wherein the tapered blood sample is positionally modulated.

4. The blood analysis system according to claim 3 wherein the tapered blood sample is rotated with respect to the optical radiation.

5. The blood analysis system according to claim 3 wherein the tapered blood sample is translated with respect to the optical radiation.

6. The blood analysis system according to claim 1 wherein the blood sample thickness is modulated.

7. A blood analysis method comprising:
- providing a blood analysis system having a monitor with a sensor port and a noninvasive optical sensor attached to the sensor port, where the optical sensor is responsive to the sensor port so as to illuminate a tissue site of a living being and detect the illumination after attenuation by pulsatile blood flow within the tissue site;
- replacing the optical sensor with a blood analysis adapter;
- collecting a blood sample from a living being with a cuvette;
- inserting the cuvette into the blood analysis adapter by positioning a cuvette in a movable drawer that is opened to receive the cuvette and closed to position the cuvette within an optical path within the blood analysis adapter; and
- analyzing the blood sample in response to signals communicated between the monitor via the sensor port.

8. The blood analysis method according to claim 7 wherein the analyzing comprises illuminating the blood sample with multiple wavelength radiation from emitters disposed within the blood analysis adapter, wherein the emitters are responsive to emitter drive signals from the sensor port.

9. The blood analysis method according to claim 8 further comprising modulating the blood sample within the cuvette.

10. The blood analysis method according to claim 9 wherein the modulating comprises:
- tapering the blood sample within the cuvette; and
- modulating the position of the cuvette with respect to the optical path.

11. The blood analysis method according to claim 9 wherein the modulating comprises modulating the thickness of the blood sample within the cuvette.

12. The blood analysis method according to claim 11 wherein the thickness modulating comprises modulating the volume of the blood sample within a flexible cuvette.

13. The blood analysis apparatus comprising functions as a non-invasive blood parameter analyzer when a monitor is coupled with an optical sensor and as an invasive blood sampler analyzer when the monitor is coupled with a blood analysis adapter, the blood analysis adapter comprises:
- an adapter body having an adapter connector and a drawer slot;
- an optical assembly enclosed within the adapter body has a transmitting assembly and a receiving assembly mounted on a circuit board;
- the optical assembly is in electrical communications with the adapter connector so as to receive emitter signals for driving emitters within the transmitting assembly and so as to transmit detector signals responsive to at least one detector in the receiving assembly;
- a drawer slidably moves within the receiving assembly so as to extend from the drawer slot in an open position and recede into the drawer slot in a closed position; and
- the drawer receives a cuvette containing a blood sample.

14. The blood analysis apparatus according to claim 13 further comprising:
- wherein the blood sample is exposed to optical radiation from the emitters;
- a cuvette pocket is defined within the drawer;
- the cuvette pocket is configured to receive a cuvette enclosed blood sample in an open position and to position the cuvette enclosed blood sample within the receiving assembly in the closed position;
- the transmitting assembly emitters generate multiple wavelength light to the receiving assembly in response to emitter signals; and
- the receiving assembly at least one detector responds to the multiple wavelength light after attenuation by the blood sample.

* * * * *

UNITED STATES PATENT AND TRADEMARK OFFICE
CERTIFICATE OF CORRECTION

| | |
|---|---|
| PATENT NO. | : 8,830,449 B1 |
| APPLICATION NO. | : 13/449307 |
| DATED | : September 9, 2014 |
| INVENTOR(S) | : Marcelo M. Lamego |

It is certified that error appears in the above-identified patent and that said Letters Patent is hereby corrected as shown below:

In the Specification

In Column 3, Line 61, change "hemaglobin" to --hemoglobin--.

In Column 7, Line 6, change "pusatile" to --pulsatile--.

In Column 11, Line 13 (Approx.), change "germanimum" to --germanium--.

In the Claims

In Column 14, Line 1, in Claim 13, change "The" to --A--.

Signed and Sealed this
Eighth Day of September, 2015

Michelle K. Lee
*Director of the United States Patent and Trademark Office*